United States Patent [19]

Shirahata et al.

[11] Patent Number: 4,691,024
[45] Date of Patent: Sep. 1, 1987

[54] NEW MITOMYCIN DERIVATIVES, PREPARATION THEREOF AND PHARMACEUTICAL COMPOSITIONS CONTAINING THEM

[75] Inventors: Kunikatsu Shirahata, Komae; Motomichi Kono; Yutaka Saito, both of Machida; Masaji Kasai, Fujisawa; Makoto Morimoto, Shizuoka; Tadashi Ashizawa, Numazu, all of Japan

[73] Assignee: Kyowa Hakko Kogyo Kabushiki Kaisha, Japan

[21] Appl. No.: 915,949

[22] Filed: Oct. 3, 1986

[30] Foreign Application Priority Data

Jun. 1, 1984 [JP] Japan ................ 59-112428

[51] Int. Cl.$^4$ .......................... C07D 487/14
[52] U.S. Cl. ................................. 548/422
[58] Field of Search ............................ 548/422

[56] References Cited

FOREIGN PATENT DOCUMENTS

| 0116208 | 8/1984 | European Pat. Off. |
| 0122797 | 9/1979 | Japan. |
| 55-45322 | 3/1980 | Japan. |
| 56-92288 | 7/1981 | Japan. |
| 0188590 | 11/1982 | Japan. |
| 0104386 | 6/1984 | Japan. |
| 59-175493 | 10/1984 | Japan. |

OTHER PUBLICATIONS

J. Med. Chem., 26, 1453–1457 (1983).
J. Am. Chem. Soc., 105, 7199 (1983).
J. Med. Chem., 24, 975–981 (1981).
J. Med. Chem., 26, 16–20 (1983).
Organic Chemistry of Bivalent Sulfur, vol. III (1960), 372 & 373.

Primary Examiner—Delbert R. Phillips
Attorney, Agent, or Firm—Wolder, Gross & Yavner

[57] ABSTRACT

The present invention provides new mitomycin derivatives of general formula (I)

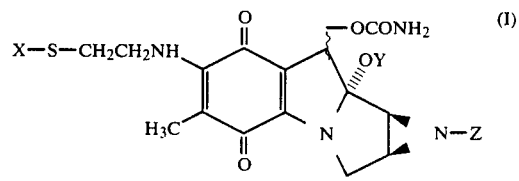

[wherein Y and Z, which may be the same or different, each represents a hydrogen atom or a methyl group; ⌇ represents $\alpha$ or $\beta$ bonding and X represents a group of formula (II)

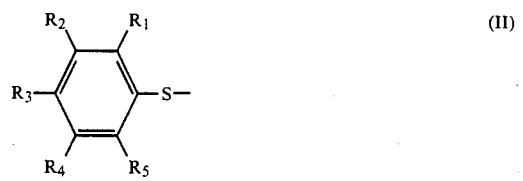

(wherein $R_1$ to $R_5$ are each selected from hydrogen, halogen, hydroxyl, nitro, amino, lower alkyl, lower alkoxy, lower alkylamino or lower alkanoylamino);
  or an S-yl group of an amino acid having a thiol group, the carboxyl group optionally being protected e.g. in the form of a lower alkyl ester group and the amino group optionally being protected e.g. in the form of a lower alkanoylamino group;
  or an S-yl group of a di- or tripeptide containing an amino acid residue with a thiol group, the carboxyl group optionally being protected e.g. in the form of a lower alkyl ester and the amino group optionally being protected e.g. in the form of a lower alkanoylamino group]; and salts thereof.

Such mitomycin derivatives have improved anti-bacterial and anti-tumor activities and low toxicity.

5 Claims, No Drawings

NEW MITOMYCIN DERIVATIVES, PREPARATION THEREOF AND PHARMACEUTICAL COMPOSITIONS CONTAINING THEM

This application is a division of application Ser. No. 740,132, filed May 31, 1985 now abandoned.

This invention relates to new mitomycin derivatives having antibacterial and anti-tumour activities, to a process for their preparation and to pharmaceutical compositions, particularly anti-tumour compositions containing them.

Mitomycin compounds are well know as antibiotics having antibacterial and anti-tumour activities. Representative known mitomycins include, for example, mitomycin A, mitomycin B, mitomycin C and porfiromycin (cf. Merck Index, 9th edition), mitomycin D and mitomycin E (Japanese Published Unexamined Patent Application No. 122797/79) and mitomycin F (Japanese Published Unexamined Patent Application No. 45322/80). Mitomycins may be produced, for example, by fermentation of *Streptomyces caespitosus*. The absolute configuration of these mitomycins has recently been revised [see K. Shirahata et al., J. Am. Chem. Soc., 105, 7199. (1983)]. The following Table 1 shows the revised chemical structures of certain mitomycins available from natural sources.

TABLE 1

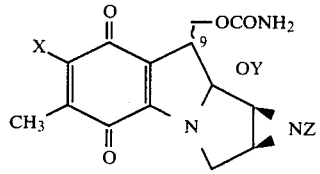

| Mitomycin | X | Y | Z | C-9 |
|---|---|---|---|---|
| A | OCH$_3$ | CH$_3$ | H | β |
| B | OCH$_3$ | H | CH$_3$ | α |
| C | NH$_2$ | CH$_3$ | H | β |
| D | NH$_2$ | H | CH$_3$ | α |
| E | NH$_2$ | CH$_3$ | CH$_3$ | α |
| F | OCH$_3$ | CH$_3$ | CH$_3$ | β |
| J | OCH$_3$ | CH$_3$ | CH$_3$ | α |
| Porfiromycin | NH$_2$ | CH$_3$ | CH$_3$ | β |

Even though mitomycins exhibit excellent anti-tumour activity, they can give rise to undesired side effects, such as decrease of leucocytes. Thus, various derivatives of mitomycin have previously been prepared which exhibit increased anti-tumour activity and/or decreased toxicity.

Derivatives of certain mitomycins have thus been prepared containing a modified 7-amino group. For example, there are known derivatives of mitomycin C and mitomycin F having a substituted 7-amino group. Such compounds are disclosed, for example, in Japanese Published Unexamined Patent Application Nos. 92288/81 and 188590/82; J. Med. Chem. 24, 975–981 (1981), ibid. 26, 16–20 (1983) and ibid. 26, 1453–1457 (1983). These prior art documents disclose that mitomycin derivatives having a modified amino group in the 7-position exhibit anti-tumour activity in vivo. Amongst the various mitomycin derivatives of this type, the following compounds may be of some interest in relation to the present invention.

Japanese Published Unexamined Patent Application No. 92288/81, discloses mitomycin derivatives wherein a 2-thiazolamino, 2-thienylmethylamino or (4-sulphonamidophenyl) methylamino group is present at the 7-position.

Japanese Published Unexamined Patent Application No. 188590/82, discloses mitomycin derivatives wherein a 2-mercaptoethylamino, 2-ethylthioethylamino, thiomorpholino, thiazolidinyl, 4-mercaptoanilino, 2-(4-methylthiazolyl)-amino, 2-(5-methyl-1,3,4-thiazolyl)amino or 4-(2,1,3-benzothiadiazolyl)amino group is present at the 7-position.

The Japanese Published Unexamined Patent Application Nos. 104386/84 (published June 16, 1984) and 175493/84 (published Oct. 4, 1984) (These applications are priority applications of EP 0116208 A1 (published Aug. 22, 1984) disclose that mitomycin derivatives having at the 7-position a group represented by the formula

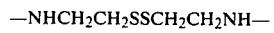
—NHCH$_2$CH$_2$SSCH$_2$CH$_2$NH— exhibit excellent antibacterial and anti-tumour activities. Examples of such derivatives are 7-N, 7'-N'-dithiodiethylenedimitomycin C; 7-N, 7'-N'-dithiodiethylenedimitomycin D; 7-N-[2-(2-hydroxyethyldithio)ethyl]mitomycin C; 7-N-[2-(2-aminoethyldithio)ethyl]mitomycin D and 7-N-2-[2,3-dihydroxypropyldithio)ethyl]mitomycin C.

The present invention provides new mitomycin derivatives having excellent antibacterial and anti-tumour activities and low toxicity.

According to one aspect of the present invention, there are provided mitomycin derivatives of general formula (I)

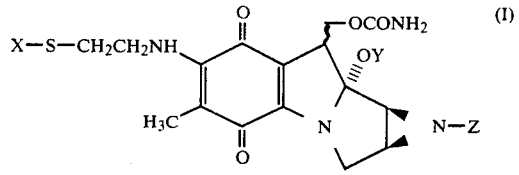

[wherein Y and Z, which may be the same or different, each represents a hydrogen atom or a methyl group; ⁓represents α or β bonding and X represents a group of formula (II)

(wherein R$_1$ to R$_5$ are each selected from hyrdogen, halogen, hydroxyl, nitro, amino, lower alkyl, lower alkoxy, lower alkylamino or lower alkanoylamino);
  or an S-yl group of an amino acid having a thiol group, the carboxyl group optionally being protected e.g. in the form of a lower alkyl ester group and the amino group optionally being protected e.g. in the form of a lower alkanoylamino group;
  or an S-yl group of a di- or tripeptide containing an amino acid residue with a thiol group, the carboxyl group optionally being protected e.g. in the form of a lower alkyl ester and the amino group optionally being protected e.g. in the form of a lower alkanoylamino group]; and salts thereof.

Mitomycin derivatives of formula (I) wherein X is a group containing a carboxyl group may for instance be in a form selected from alkali metal salts, e.g. the sodium or potassium salt, ammonium salts and organic amine addition salts. Preferred examples of organic amines which may be used include triethylamine and pyridine.

With regard to the definition of $R_1$ to $R_5$ in formula (II), one or more of $R_1$ to $R_5$ may be a straight or branched lower (e.g. $C_{1-5}$) alkyl group, for example methyl, ethyl, n-propyl, n-butyl or n-pentyl. Suitable lower alkoxy groups for $R_1$ to $R_5$ include alkoxy groups having 1–3 carbon atoms such as methoxy, ethoxy or i-propoxy. Lower alkylamino groups from which $R_1$ to $R_5$ may be selected include alkylamino groups having 1–3 carbon atoms such as methylamino or ethylamino. Suitable lower alkanoylamino groups for $R_1$ to $R_5$ include alkanoylamino groups having 1–4 carbon atoms such as formamido, acetamido and n-propionamido. One or more of $R_1$ to $R_5$ may be a halogen atom, e.g. a fluorine, chlorine or bromine atom.

Preferred mitomycin derivatives according to the invention containing a group of formula (II) are those (a) wherein either one of $R_1$ to $R_5$ or two of $R_1$ to $R_5$, which may be the same or different, is/are selected from hydroxy, nitro, amino, lower alkyl, lower alkoxy, lower alkylamino or lower alkanoylamino and the remaining R groups are hydrogen atoms; and (b) wherein one or more of $R_1$ to $R_5$ are halogen atoms and any remaining R groups are hydrogen atoms.

Suitable groups of formula (II)

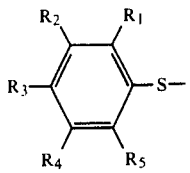

(II)

are exemplified by phenylthio, 2-aminophenylthio, 3-aminophenylthio, 4-aminophenylthio, 3,4-diaminophenylthio, 2-acetamidophenylthio, 3-acetamidophenylthio, 4-acetamidophenylthio, 4-acetamido-3-aminophenylthio, 3-acetamido-4-aminophenylthio, 4-nitrophenylthio, 2-methoxyphenylthio, 3-methoxyphenylthio, 4-methoxyphenylthio, 4-ethoxyphenylthio, 4-methylphenylthio, 4-ethylphenylthio, 2-chlorophenylthio, 4-chlorophenylthio, 2-bromophenylthio, 4-bromophenylthio, 4-fluorophenylthio, 2,5-dichlorophenylthio, 2,6-dichlorophenylthio, 3,4-dichlorophenylthio, 2,4,5-trichlorophenylthio, 2,3,5,6-tetrafluorophenylthio, 4-hydroxyphenylthio and 3,4-dihydroxyphenylthio groups.

With respect to the definition of X in formula (I), preferred amino acids having a thiol group and preferred di- or tripeptides containing an amino acid residue with a thiol group are exemplified by cysteine, homocysteine, cysteamine, penicillamine, asparaginocysteine, glutaminocysteine, glycinocysteine, phenylalaninocysteine, tyrosinocysteine, and glutathione.

A selected amino acid or the amino acid residues of a selected di- or tripeptide may be in the L, D or DL forms. Lower alkyl groups which may preferably be used to esterify and protect the carboxyl group of a selected amino acid or selected di- or tripeptide are exemplified by a methyl or ethyl group. Suitable lower alkanoyl groups for the protection of the amino group are exemplified by alkanoyl groups having 1–3 carbon atoms, for example, a formyl or acetyl group. Other carboxyl and amino protecting groups may of course be used, subject to their physiological acceptability.

Preferred S-yl groups of amino acids having a thio group and di- or tripeptides containing such an amino acid are exemplified by L-cystein-S-yl, D-cystein-S-yl, L-homocystein-S-yl, D-homocystein-S-yl, L-1-methoxycarbonylcysteamin-S-yl, D-1-methoxycarbonylcysteamin-S-yl, L-1-ethoxycarbonylcysteamin-S-yl, D-1-ethoxycarbonylcysteamin-S-yl, L-penicillamin-S-yl, D-penicillamin-S-yl, N-acetyl-L-cystein-S-yl, N-acetyl-D-cysteamin-S-yl, N-acetyl-L-penicillamin-S-yl, N-acetyl-D-penicillamin-S-yl, L-asparagino-L-cystein-S-yl, L-glutamino-L-cystein-S-yl, glycino-L-cystein-S-yl, L-phenylalanino-L-cystein-S-yl, L-tyrosino-L-cystein-S-yl, α-L-glutamyl-L-cystein-S-yl, γ-L-glutamyl-L-cystein-S-yl, L-glutaminyl-L-cystein-S-yl, L-tyrosyl-L-cystein-S-yl, glycyl-L-cystein-S-yl, L-asparagyl-L-cystein-S-yl, L-alanyl-L-cystein-S-yl, γ-L-glutamyl-L-cysteinylglycin-S-yl (the S-yl group of glutathione), γ-L-glutamyl-L-cysteinyl-ethyl-glycinat-S-yl, glycyl-L-alanyl-L-cystein-S-yl, α-L-glutamyl-L-cysteinylglycin-S-yl and L-asparagyl-L-cysteinylglycin-S-yl.

Mitomycin derivatives of the formula (I) as hereinbefore defined, may be obtained by a process which comprises reacting a compound of formula (III)

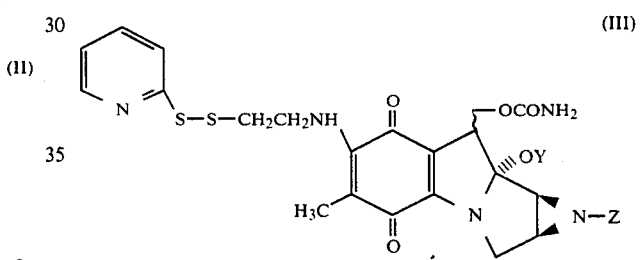

(III)

(wherein Y, Z and ⁓ are as hereinbefore defined) with a compound of formula (IV)

X - H    (IV)

(wherein X is as hereinbefore defined) or, if X contains a carboxyl group, a corresponding alkali metal salt in the presence of inert solvent.

Compounds of formula (III) may be produced by the method disclosed in EP 0116208 A1. Suitable alkali metal salts of compounds of formula (IV) wherein X contains a carboxyl group include, for example, the sodium salt and the potassium salt.

Inert solvents which may be used for the process of the present invention include, for example, lower alkanols (e.g. $C_{1-4}$) such as methanol, ethanol and isopropanol; halogenated lower alkanes, such as chloroform, dichloromethane, and dichloroethane; acetonitrile, dimethylformamide, dimethyl sulfoxide and water. Such solvents may be used alone or in combination.

Although the reaction temperature and time may vary with different compounds of formula (IV), the reaction may usually be effected at a temperature of 0°–30° C. for from several minutes to several hours.

Treatment after completion of the reaction may vary, depending upon the solubility of the reaction product. When the product is insoluble or hardly soluble in water, the reaction solution may be directly concentrated under reduced pressure. Alternatively, it is possible to extract the product with chloroform or ethyl acetate and concentrate the extract under reduced pressure, followed by purification. When the product is water-soluble, the product may be directly purified, although it is possible to add chloroform or ethyl acetate to the reaction solution, extract the reaction solution with water and then concentrate the extract, i.e. the aqueous layer under reduced pressure, followed by purification. In all cases, purification may be effected, for example, by column chromatography, thin layer chromatography or recrystallization.

The above-mentioned procedure is disclosed in EP 0116208 A1.

Mitomycin derivatives of formula (I), as hereinbefore defined, and physiologically acceptable salts thereof may be used as antibacterial and anti-tumour agents owing to their excellent antibacterial and anti-tumour activities.

Thus, according to a further feature of the present invention, there are provided pharmaceutical compositions containing as active ingredient at least one mitomycin derivative of formula (I) or a physiologically acceptable salt thereof in association with one or more pharmaceutical carriers and/or excipients. Preferred mitomycin derivatives of formula (I) and physiologically acceptable salts thereof for use as medicaments are those with high water solubility. High water solubility is exhibited by mitomycin derivatives of formula (I) wherein X is an S-yl group of an amino acid having a thiol group, the carboxyl group optionally being protected e.g. in the form of a lower alkyl ester group and the amino group optionally being protected e.g. in the form of a lower alkanoylamino group, or an S-yl group of a di- or tripeptide containing an amino acid residue with a thiol group, the carboxyl group optionally being protected e.g. in the form of a lower alkyl ester and the amino group optionally being protected e.g. in the form of a lower alkanoylamino group]; or salts thereof selected from alkali metal salts, ammonium salts and organic amine addition salts. Especially high water solubility is exhibited by mitomycin derivatives of formula (I) wherein X is an S-yl group of an amino acid having a thiol group, or an S-yl group of a di- or tripeptide containing an amino acid residue with a thiol group (namely the case when any carboxyl group and amino group of the amino acid or di- or tripeptide are not protected); or salts thereof selected from alkali metal salts, ammonium salts and organic amine addition salts.

For use as, for example, anti-tumour agents, mitomycin derivatives of formula (I) may be dissolved, for example, in physiological saline solution, or a glucose, lactose or mannitol injection solution. Administration may, for example, be effected by intravenous injection at a dose of 0.02–1 mg/kg of body weight. Compounds of formula (I) may be freeze-dried in accordance with the Pharmacopoeia of Japan and a dry powder injectable formulation may be prepared with addition of sodium chloride. The anti-tumour agent may further contain therein well-known, pharmacologically acceptable diluent(s), adjuvant(s) and/or carrier(s) such as salts which fulfil pharmaceutical utility. The dose required of a pharmaceutical composition according to the invention may be varied depending upon, for example, the age and symptoms of each patient. The administration schedule may be varied depending upon the dose. Thus, administration may be effected, for example, once a week or once a three weeks. If desired, oral administration is also possible, e.g. using the above doses, for which purpose tablets, powders and granules containing appropriate excipients may for example be used. If desired, intraarterial, intraperitoneal and intrapleural administrations may also be used.

The following non-limiting examples illustrate the present invention.

EXAMPLE 1

7-N-[2-(Phenyldithio)ethyl]mitomycin C (Compound 1)

70 mg of 7-N-[2-(2-pyridyldithio)ethyl]mitomycin C (disclosed in EP 0116208 A1 is dissolved in 2 ml of methanol. To this solution, 14.2 $\mu$l of thiophenol is added while stirring the solution at room temperature. About 2 minutes after this, chloroform (30 ml) is added and the mixture is washed with an aqueous solution of sodium bicarbonate and then with an aqueous solution of sodium chloride. The mixture is then dried over anhydrous sodium sulfate. Chloroform is removed from the mixture by distillation under reduced pressure. The residue is purified by silica gel column chromatography. Bluish fractions eluted with a mixture of chloroform/methanol (97:3 v/v) are collected and combined, from which the solvent is removed by distillation under reduced pressure. The residue is dissolved in a small amount of chloroform. The solution is dropped into cyclohexane to result in a grayish blue precipitate which is then separated by filtration to obtain 64 mg of Compound 1.

Elementary analysis (%): C 54.8, H 5.0, N 10.9 Calculated as $C_{23}H_{26}N_4O_5S_2$: C 55.0, H 5.2, N 11.2

$^1$H-NMR (CDCl$_3$, $\delta$): 1.90(3H,s), 2.85(2H, m), 2.89 (2H, t), 3.21(3H, s), 3.50(1H, dd), 3.60(1H, dd), 3.81(2H, q), 4.26(1H, d), 4.50(1H, dd), 4.71 (2H, br.s), 4.71(1H, dd), 6.36(1H, br.), 7.20–7.58(5H, m)

IR (KBr, cm$^{-1}$): 3290, 2930, 1720, 1632, 1558, 1510, 1449, 1328, 1061

EXAMPLE 2

7-N-[2-(2-Aminophenyldithio)ethyl]mitomycin C (Compound 2)

A similar procedure to that described in Example 1 is effected using 70 mg of 7-N-[2-(2-pyridyldithio)ethyl]-mitomycin C and 17.2 mg of 2-aminothiophenol to obtain 35.7 mg of Compound 2 as a grayish blue powder with a yield of 49.6%.

Elementary analysis (%): C 53.1, H 5.2, N 13.3 Calculated as $C_{23}H_{27}N_5O_5S_2$: C 53.4, H 5.3, N 13.5

$^1$H-NMR (CDCl$_3$, $\delta$): 1.95(3H, s), 2.86(2H, m), 2.92 (2H, t), 3.21(3H, s), 3.50(1H, dd), 3.59(1H, dd), 3.88(2H, q), 4.27(1H, d), 4.50(1H, dd), 4.72(1H, dd), 4.75(2H, br.), 6.37(1H, br.t), 6.67(2H, m), 7.15(1H, m), 7.39(1H, dd)

IR (KBr, cm$^{-1}$): 3290, 2930, 1713, 1631, 1610, 1551, 1508, 1475, 1445, 1328, 1061, 752

EXAMPLE 3

7-N-[2-(3-aminophenyldithio)ethyl]mitomycin C (Compound 3)

A similar procedure to that described in Example 1 is effected using 70 mg of 7-N-[2-(2-pyridyldithio)ethyl]-mitomycin C and 14.5 $\mu$l of 3- aminothiophenol to obtain 52.2 mg of Compound 3 as a grayish blue powder with a yield of 72.6%.

Elementary analysis: C 53.1, H 5.1, N 13.2 Calculated as $C_{23}H_{27}N_5O_5S_2$: C 53.4, H 5.3, N 13.5

¹H-NMR (CDCl₃, δ): 1.91(3H, s), 2.81(1H, dd), 2.84 (1H, d), 2.91(2H, t), 3.21(3H, s), 3.50(1H, dd), 3.59(1H, dd), 3.80(2H, q), 4.27(1H, d), 4.48 (1H, dd), 4.60(1H, dd), 4.77(2H, br.), 6.42(1H, br.), 6.50(1H, m), 6.76–6.93(2H, m), 7.06(1H, t)

IR (KBr, cm$^{-1}$): 3300, 2940, 1706, 1631, 1591, 1552, 1510, 1478, 1448, 1329, 1063, 758, 688

EXAMPLE 4

7-N-[2-(4-aminophenyldithio)ethyl]mitomycin C (Compound 4)

A similar procedure to that described in Example 1 is effected using 70 mg of 7-N-[2-(2-pyridyldithio)ethyl]-mitomycin C and 18 mg of 4-aminothiophenol to obtain 63.6 mg of Compound 4 as a grayish blue powder with a yield of 88.4%.

Elementary analysis (%): C 53.1, H 5.0, N 13.2 Calculated as $C_{23}H_{27}N_5O_5S_2$: C 53.4, H 5.3, N 13.5

¹H-NMR (CDCl₃, δ): 1.88(3H, s), 2.91(3H, m), 3.20 (3H, s), 3.50(1H, dd), 3.60(1H, dd), 3.81(2H, q), 4.28(1H, d), 4.58(1H, dd), 4.76(1H, dd), 4.79 (2H, br.), 6.34(1H, br.), 6.48–7.34(4H, AA'BB')

IR (KBr, cm$^{-1}$): 3360, 3300, 2940, 1711, 1631, 1595, 1551, 1509, 1492, 1449, 1329, 1062

EXAMPLE 5

7-N-[2-(4-Acetamidophenyldithio)ethyl]mitomycin C (Compound 5)

A similar procedure to that described in Example 1 is effected using 50 mg of 7-N-[2-(2-pyridyldithio)ethyl]-mitomycin C and 17 mg of 4-mercaptoacetanilide) to obtain 38 mg of Compound 5 as a grayish blue powder with a yield of 68.4%.

Elementary analysis (%): C 53.4, H 5.0, N 12.3 Calculated as $C_{25}H_{29}N_5O_6S_2$: C 53.7, H 5.2, N 12.5

¹H-NMR (C₅D₅N, δ): 2.06(3H, s), 2.16(3H, s), 2.75 (1H, br.d), 3.03(2H, t), 3.15(1H, d), 3.23(3H, s), 3.59(1H, br.d), 3.90(2H, q), 3.99(1H, dd), 4.52(1H, d), 5.04(1H, dd), 5.39(1H, dd), 7.13 (1H, br.t), 7.66(2H, br.s), 7.59–8.03(4H, AA'BB'), 10.76(1H, br.s)

IR (KBr, cm$^{-1}$): 3290, 1713, 1633, 1589, 1533, 1510, 1323, 1062, 755

EXAMPLE 6

7-N-[2-(4-Acetamidophenyldithio)ethyl]porfiromycin (Compound 6)

A similar procedure to that described in Example 1 is effected using 70 mg of 7-N-[2-(2-pyridyldithio)ethyl]-porfiromycin (disclosed in EP 0116208 A1) and 22 mg of 4-mercaptoacetanilide to obtain 60.8 mg of Compound 6 as a grayish blue powder with a yield of 78.4%.

Elementary analysis (%): C 54.1, H 5.3, N 12.0 Calculated as $C_{26}H_{31}N_5O_6S_2$: C 54.4, H 5.5, N 12.2

¹H-NMR (CDCl₃, δ): 1.88(3H, s), 2.16(3H, s), 2.27 (3H, s), 2.27(2H, m), 2.94(2H, t), 3.17(3H, s), 3.46(1H, dd), 3.55(1H, dd), 3.77(2H, q), 4.23 (1H, d), 4.31(1H, dd), 4.73(1H, dd), 4.80(2H, br.), 6.36(1H, br.), 7.45(4H, AA'BB'), 7.94(1H, br.s)

IR (KBr, cm$^{-1}$): 3310, 2930, 1712, 1679, 1635, 1590, 1554, 1551, 1449, 1397, 1325, 1315, 1061

EXAMPLE 7

7-N-[2-(4-Acetamidophenyldithio)ethyl]mitomycin D (Compound 7)

A similar procedure to that described in Example 1 is effected using 70 mg of 7-N-[2-(2-pyridyldithio)ethyl]-mitomycin D (disclosed in EP 0116208 A1 and 23 mg of 4-mercaptoacetanilide to obtain 59.8 mg of Compound 7 as a grayish blue powder.

Elementary analysis (%): C 53.6, H 5.0, N 12.2 Calculated as $C_{25}H_{29}N_5O_6S_2$: C 53.7, H 5.2, N 12.5

¹H-NMR (CDCl₃, δ): 1.70(3H, s), 2.11(3H, s), 2.29 (5H, s), 3.04(2H, m), 3.49(1H, d), 3.69(3H, m), 4.03(1H, d), 4.78(2H, m), 5.15(2H, br.), 6.23 (1H, br.), 7.42(4H, s), 7.76(1H, br.s)

IR (KBr, cm$^{-1}$): 3300, 1707, 1630, 1590, 1510, 1450, 1330.

EXAMPLE 8

7-N-[2-(4-Nitrophenyldithio)ethyl]mitomycin C (Compound 8)

A similar procedure to that described in Example 1 is effected using 70 mg of 7-N-[2-(2-pyridyldithio)ethyl]-mitomycin C and 21 mg of 4-nitrothiophenol to obtain 65.3 mg of Compound 8 as a grayish blue powder (Yield: 85.8%).

Elementary analysis (%): C 50.2, H 4.8, N 12.5 Calculated as $C_{23}H_{25}N_5O_7S_2$: C 50.5, H 4.6, N 12.8

¹H-NMR (CDCl₃, δ): 1.90(3H, s), 2.84(2H, br.), 2.94 (2H, t), 3.21(3H, s), 3.50(1H, dd), 3.60(1H, dd), 3.82(2H, q), 4.24(1H, d), 4.49(1H, dd), 4.72(1H, dd), 4.74(2H, br.), 6.37(1H, br.), 7.55–8.26(4H, AA'BB')

IR (KBr, cm$^{-1}$): 3290, 2930, 1720, 1632, 1545, 1510, 1446, 1339, 1061, 852, 759, 741

EXAMPLE 9

7-N-[2-(4-Methoxyphenyldithio)ethyl]mitomycin C (Compound 9)

A similar procedure to that described in Example 1 is effected by the use of 70 mg of 7-N-[2-(2-pyridyldithio)ethyl]mitomycin C and 19 mg of 4-methoxythiophenol to obtain 69.4 mg of Compound 9 as a grayish blue powder.

Elementary analysis (%): C 54.1, H 5.2, N 10.3 Calculated as $C_{24}H_{28}N_4O_6S_2$: C 54.1, H 5.3, N 10.5

¹H-NMR (CDCl₃, δ): 1.94(3H, s), 2.81(1H, br.), 2.88 (2H, t), 2.89(1H, br.), 3.21(3H, s), 3.51(1H, dd), 3.60(1H, dd), 3.79(3H, s), 3.83(2H, q), 4.27(1H, d), 4.49(1H, dd), 4.72(1H, dd), 4.72 (2H, br.), 6.38(1H, br.), 6.80–7.52(4H, AA'BB')

IR (KBr, cm$^{-1}$): 3290, 2930, 1719, 1632, 1590, 1556, 1508, 1491, 1449, 1327, 1246, 1061

EXAMPLE 10

7-N-[2-(4-Methylphenyldithio)ethyl]mitomycin C (Compound 10)

A similar procedure to that described in Example 1 is effected using 70 mg of 7-N-[2-(2-pyridyldithio)-ethyl]-mitomycin C and 17 mg of 4-thiocresol to obtain 52.3 mg of Compound 10 as a grayish blue powder with a yield of 72.8%.

Elementary analysis (%): C 55.7, H 5.6, N 10.6 Calculated as $C_{24}H_{28}N_4O_5S_2$: C 55.8, H 5.5, N 10.8

¹H-NMR (CDCl₃, δ): 1.91(3H, s), 2.32(3H, s), 2.79–2.92(2H, m), 2.88(2H, t), 3.21(3H, s), 3.50(1H, dd), 3.60(1H, dd), 3.81(2H, q), 4.27(1H, d), 4.50(1H, dd), 4.70(2H, br.), 4.71(1H, dd), 6.46(1H, br.), 7.08–7.46(4H, AA'BB')

IR (KBr, cm$^{-1}$): 3290, 2930, 1717, 1632, 1554, 1508, 1447, 1328, 1061

EXAMPLE 11

7-N-[2-(4-Chlorophenyldithio)ethyl]mitomycin C (Compound 11)

A similar procedure to that described in Example 1 is effected using 70 mg of 7-N-[2-(2-pyridyldithio)ethyl]mitomycin C and 20 mg of 4-chlorothiophenol to obtain 45.1 mg of Compound 11 as a grayish blue powder with a yield of 60.2%.

Elementary analysis (%): C 51.4, H 4.7, N 10.2 Calculated as $C_{23}H_{25}ClN_4O_5S_2$: C 51.4, H 4.7, N 10.4

$^1$H-NMR (CDCl$_3$, δ): 1.91(3H, s), 2.85(2H, m), 2.89 (2H, t), 3.21(3H, s), 3.50(1H, dd), 3.60(1H, dd), 3.80(2H, q), 4.27(1H, d), 4.49(1H, dd), 4.72 (1H, dd), 4.74(2H, br.), 6.37(1H, br.), 7.24–7.43 (4H, AA'BB')

IR (KBr, cm$^{-1}$): 3290, 2930, 1717, 1632, 1556, 1510, 1471, 1449, 1327, 1062

EXAMPLE 12

7-N-[2-(4-Fluorophenyldithio)ethyl]mitomycin C (Compound 12)

A similar procedure to that described in Example 1 is effected using 70 mg of 7-N-[2-(2-pyridyldithio)ethyl]mitomycin C and 17 mg of 4-fluorothiophenol to obtain 51.5 mg of Compound 12 as a grayish blue powder with a yield of 71.2%.

Elementary analysis (%): C 53.2, H 4.7, N 10.5 Calculated as $C_{23}H_{25}FN_4O_5S_2$: C 53.1, H 4.8, N 10.8

$^1$H-NMR (CDCl$_3$, δ): 1.93(3H, s), 2.81(1H, dd), 2.89(1H, d), 2.89(2H, t), 3.21(3H, s), 3.50(1H, dd), 3.60(1H, dd), 3.82(2H, q), 4.26(1H, d), 4.49(1H, dd), 4.72(1H, dd), 4.74(2H, br.), 6.37 (1H, br.), 7.03(2H, m), 7.51(2H, m)

IR (KBr, cm$^{-1}$): 3300, 2940, 1718, 1632, 1557, 1510, 1488, 1450, 1328, 1220, 1061

EXAMPLE 13

7-N-[2-(2,3,5,6-Tetrafluorophenyldithio)ethyl]mitomycin C (Compound 13)

70 mg of 7-N-[2-(2-pyridyldithio)ethyl]mitomycin C is dissolved in 2 ml of methanol. To this solution is added 25 μl of 2,3,5,6-tetrafluorothiophenol at 0° C. while stirring. About 2 minutes later, the solvent is distilled off under reduced pressure, and the residue is subjected to silica gel chromatography. The fraction eluted with chloroform/methanol (94:6 v/v) is concentrated under reduced pressure and then purified by silica gel thin layer chromatography (TLC). By developing with ethyl acetate/methanol (98:2 v/v), a purple compound having an Rf value of 0.38 is recovered, which is then powderized by using a mixed solvent of chloroform/cylohexane to obtain 27.6 mg of Compound 13 as a purple powder (Yield: 34.6%).

Elementary analysis (%): C 47.8, H 4.0, N 9.5 Calculated as $C_{23}H_{22}F_4N_4O_5S_2$: C 48.1, H 3.9, N 9.8

$^1$H-NMR (CDCl$_3$, δ): 2.02(3H, s), 2.84(1H, dd), 2.90 (1H, d), 3.01(2H, t), 3.22(3H, s), 3.51(1H, dd), 3.60(1H, dd), 3.94(2H, q), 4.27(1H, d), 4.50 (1H, dd), 4.71(1H, dd), 4.71(2H, br.), 6.35(1H, br.), 7.16(1H, tt)

IR (KBr, cm$^{-1}$): 3440, 3300, 1718, 1703, 1632, 1563, 1491, 1330, 1061, 918, 852, 711

EXAMPLE 14

7-N-[2-[(L-Cystein-S-yl)thio]ethyl]mitomycin C (Compound 14)

70 mg of 7-N-[2-(2-pyridyldithio)ethyl]mitomycin C is dissolved in 2 ml of methanol. To this solution, 2 ml of an aqueous solution containing 16 mg of L-cysteine is added dropwise while stirring the solution at 0° C. About 5 minutes later, water (4 ml) is added to the mixture, which is then passed through a column packed with Diaion HP 20 (commercial product of Mitsubishi Kasei K.K., Japan) as a carrier. The column is washed with water. Fractions eluted with a mixture of water/methanol (4:6 v/v) are collected, combined and concentrated under reduced pressure. The concentrate is freeze-dried to obtain 35.8 mg of Compound 14 as a green powder (Yield: 50.1%).

Elementary analysis (%): C 46.7, H 5.3, N 13.2 Calculated as $C_{20}H_{27}N_5O_7S_2 \cdot 1/2H_2O$: C 46.0, H 5.4, N 13.4

$^1$H-NMR (CD$_3$OD, δ): 2.00(3H, s), 2.80–3.07(6H, m), 3.22(3H, s), 3.26–3.64(2H, m), 3.82–4.02(3H, m), 4.17(1H, d), 4.24(1H, dd), 4.68(1H, dd)

IR (KBr, cm$^{-1}$): 3290, 3190, 2940, 1709, 1631, 1551, 1509, 1449, 1331, 1063

EXAMPLE 15

7-N-[2-[(L-Cystein-S-yl)thio]ethyl]mitomycin D (Compound 15)

70 mg of 7-N-[2-(2-pyridyldithio)ethyl]mitomycin D and 16 mg of L-cysteine are treated in a similar manner to that described in Example 14 to obtain Compound 15 (33.3 mg) as a grayish green powder with a yield of 46.6%.

Elementary analysis (%): C 46.8, H 5.5, N 13.4 Calculated as $C_{20}H_{27}N_5O_7S_2$: C 46.8, H 5.3, N 13.6

$^1$H-NMR (D$_2$O, δ): 1.98(3H, s), 2.30(3H, s), 2.59(1H, d), 2.70(1H, dd), 2.96–3.44(4H, m), 3.64(1H, dd), 3.72(1H, dd), 3.99–4.15(4H, m), 4.38(1H, dd), 4.69(1H, dd)

IR (KBr, cm$^{-1}$): 3300, 3190, 2960, 2920, 1706, 1630, 1548, 1509, 1477, 1413, 1334, 1140, 1112, 1061, 994

EXAMPLE 16

7-N-[2-[(L-1-Methoxycarbonylcysteamin-S-yl)thio]ethyl]mitomycin C (Compound 16)

70 mg of 7-N-[2-(2-pyridyldithio)ethyl]mitomycin C is dissolved in 2 ml of methanol. To this solution is added dropwise 1 ml of methanol containing 23 mg of L-cysteine methyl ester hydrochloride and 50 μl of triethylamine. About 2 minutes later, the solvent is removed from the mixture by distillation under reduced pressure. Then, a similar treatment to that described in Example 1 is effected to obtain a small amount of Compound 16 as a grayish green powder. The yield of the resultant compound is not constant because of its unstability.

Elementary analysis (%): C 47.5, H 5.3, N 13.0 Calculated as $C_{21}H_{29}N_5O_7S_2$: C 47.8, H 5.5, N 13.3

$^1$H-NMR (CDCl$_3$, δ): 2.02(3H, s), 2.79–3.08(6H, m), 3.21(3H, s), 3.51(1H, dd), 3.59(1H, dd), 3.75 (3H, s), 3.81(1H, m), 3.88(2H, q), 4.27(1H, d), 4.47(1H, dd), 4.70(1H, dd), 4.91(2H, br.), 6.48(1H, br.t)

IR (KBr, cm$^{-1}$): 3300, 2960, 1721, 1631, 1554, 1508, 1448, 1329, 1062

EXAMPLE 17

7-N-[2-[L-1-Ethoxycarbonylcysteamin-S-yl)thio]ethyl]mitomycin C (Compound 17)

A similar procedure to that described in Example 16 is effected using 70 mg of 7-N-[2-(2-pyridyldithio)ethyl]mitomycin C and 25 mg of L-cysteine ethyl ester hydrochloride to obtain a small amount of Compound 17 as a grayish green powder. The yield is not constant because of unstability of the product.

Elementary analysis (%): C 48.7, H 5.8, N 12.7 Calculated as $C_{22}H_{31}N_5O_7S_2$: C 48.8, H 5.8, N 12.9

$^1$H-NMR (CDCl$_3$, δ): 1.29(3H, t), 2.03(3H, s), 2.75–3.19(4H, m), 2.90(2H, t), 3.21(3H, s), 3.50(1H, dd), 3.60(1H, dd), 3.79(1H, m), 3.88(2H, q), 4.21(2H, q), 4.27(1H, d), 4.49(1H, dd), 4.71 (1H, dd), 4.79(2H, br.), 6.48(1H, br.t)

IR (KBr, cm$^{-1}$): 3290, 2930, 1722, 1633, 1553, 1507, 1446, 1327, 1061

EXAMPLE 18

7-N-[2-[(L-Pencillamin-S-yl)thio]ethyl]mitomycin C (Compound 18)

A similar procedure to that described in Example 14 is effected using 70 mg of 7-N-[2-(2-pyridyldithio)ethyl]mitomycin C and 20 mg of L-penicillamine to obtain 48.2 mg of Compound 18 as a grayish green powder with a yield of 64%.

Elementary analysis (%): C 49.0, H 5.5, N 12.7 Calculated as $C_{22}H_{31}N_5O_7S_2$: C 48.8, H 5.8, N 12.9

$^1$H-NMR (D$_2$O, δ): 1.37(3H, s), 1.54(3H, s), 1.98(3H, s), 3.05(5H, m), 3.29(3H, s), 3.62(1H, dd), 3.63(1H, dd), 3.84(1H, s), 4.01(2H, t), 4.18 (1H, d), 4.24(1H, dd), 4.60(1H, dd)

IR (KBr, cm$^{-1}$): 3430, 3290, 2970, 1709, 1632, 1551, 1510, 1450, 1335, 1064

EXAMPLE 19

7-N-[2-[(N-Acetyl-L-cystein-S-yl)thio]ethyl]mitomycin C potassium salt (Compound 19)

2 ml of methanol containing 70 mg of 7-N-[2-(2-pyridyldithio)ethyl]mitomycin C is stirred at 0° C. To this solution is added dropwise an aqueous solution (1 ml) containing 22 mg of N-acetyl-L-cysteine and 40 mg of potassium bicarbonate. After additional stirring for about 5 minutes, water is added to the solution, which is then passed through a column packed with Diaion HP 20 as a carrier. Fractions obtained by elution with a mixture of water/methanol (7:3 v/v) are collected, combined and freeze-dried to obtain 40 mg of Compound 19 as a grayish blue powder with a yield of 48.5%.

Elementary analysis (%): C 44.3, H 5.0, N 11.5 Calculated as $C_{22}H_{28}KN_5O_8S_2$: C 44.5, H 4.8, N 11.8

$^1$H-NMR (D$_2$O, δ): 1.97(3H, s), 2.04(3H, s), 3.27(3H, s), etc.

IR (KBr, cm$^{-1}$): 3270, 3200, 2910, 1711, 1613, 1555, 1510, 1327, 1138, 1061

EXAMPLE 20

7-N-[2-[(Glycino-L-cystein-S-71)thio]ethyl]mitomycin C (Compound 20)

A similar procedure to that described in Example 14 is effected using 70 mg of 7-N-[2-(2-pyridyldithio)ethyl]mitomycin C and 17 mg of L-cysteinylglycine to obtain 63.1 mg of Compound 20 as a grayish green powder with a yield of 79.6%.

Elementary analysis (%): C 46.4, H 5.4, N 14.4 Calculated as $C_{22}H_{30}N_6O_8S_2$: C 46.3, H 5.3, N 14.7

$^1$H-NMR (D$_2$O, δ): 1.90(3H, s), 2.91–3.15(6H, m), 3.21(3H, s), 3.43–3.62(2H, m), 3.74(2H, AB), 3.81–4.04(3H, m), 4.15–4.31(2H, m), 4.52(1H, dd)

IR (KBr, cm$^{-1}$): 3290, 2940, 1710, 1631, 1551, 1510, 1445, 1328, 1061

EXAMPLE 21

7-N-[2-[(Glycino-L-cystein-S-yl)thio]ethyl]mitomycin D (Compound 21)

A similar procedure to that described in Example 14 is effected using 70 mg of 7-N-[2-(2-pyridyldithio)ethyl]mitomycin D and 17 mg of L-cysteinylglycine to obtain 57.6 mg of Compound 21 as a grayish green powder with a yield of 72.6%.

Elementary analysis (%): C 45.0, H 5.3, N 14.0 Calculated as $C_{22}H_{30}N_6O_8S_2 \cdot H_2O$: C 44.9, H 5.5, N 14.3

$^1$H-NMR (D$_2$O, δ): 1.96(3H, s), 2.30(3H, s), 2.59 (1H, d), 2.71(1H, dd), 2.95–3.42(4H, m), 3.55–3.74(2H, m), 3.81(2H, AB), 4.02–4.14(3H, m), 4.31(1H, m), 4.39(1H, dd), 4.68(1H, dd)

IR (KBr, cm$^{-1}$): 3280, 2940, 1695, 1627, 1544, 1511, 1450, 1400, 1331

EXAMPLE 22

7-N-[2-[(γ-L-Glutamyl-L-cysteinylglycin-S-yl)thio]ethyl]mitomycin C potassium salt (Compound 22)

A similar procedure to that described in Example 19 is effected using 70 mg of 7-N-[2-(2-pyridyldithio)ethyl]mitomycin C and 42 mg of glutathione to obtain 55.0 mg of Compound 22 as a bluish paste (Yield: 53.6%).

Elementary analysis (%): C 43.7, H 5.1, N 13.0 Calculated as $C_{27}H_{36}KN_7O_{11}S$: C 44.0, H 4.9, N 13.3

$^1$H-NMR (D$_2$O, δ): 1.96(3H, s), 3.27(3H, s) etc.

IR (KBr, cm$^{-1}$): 3410, 3190, 3070, 2940, 1710, 1632, 1604, 1553, 1508, 1330, 1137, 1064

EXAMPLE 23

7-N-[2-[(γ-L-glutamyl-L-cysteinylglycin-S-yl)thio]ethyl]-mitomycin D potassium salt (Compound 23)

A similar procedure to that described in Example 19 is effected using 70 mg of 7-N-[2-(2-pyridyldithio)ethyl]mitomycin D and 42 mg of glutathione to obtain 73.3 mg of Compound 23 as a grayish green powder with a yield of 71.5%.

Elementary analysis (%): C 44.1, H 4.9, N 13.0 Calculated as $C_{27}H_{36}KN_7O_{11}S_2$: C 44.0, H 4.9, N 13.3

$^1$H-NMR (D$_2$O, δ): 1.97(3H, s), 2.30(3H, s) etc.

IR (KBr, cm$^{-1}$): 3270, 1707, 1628, 1547, 1508, 1448, 1430, 1335, 1138

EXAMPLE 24

7-N-[2-[(DL-Homocystein-S-yl)thio]ethyl]mitomycin C (Compound 24)

100 mg of 7-N-[2-(2-pyridyldithio)ethyl]mitomycin C is dissolved in 5 ml of methanol and 5 ml of an aqueous solution containing 26.8 mg of DL-homocysteine is added dropwise to the solution. 20 minutes later, 15 ml of water is added to the solution and the mixture is passed through a column packed with Diaion HP 20 as a carrier. After washing with water, elution is effected with a mixture of water/methanol (45:55 v/v), and the eluted fractions are collected, combined and concentrated under reduced pressure. The concentrate is freeze-dried to obtain 11.6 mg of Compound 24 as a grayish blue powder with a yield of 11.1%.

Elementary analysis (%): C 48.1, H 5.8, N 13.2 Calculated as $C_{21}H_{29}N_5O_7S_2$: C 47.8, H 5.5, N 13.3

$^1$H-NMR (D$_2$O, δ): 1.96(3H, s), 2.24(2H, m), 2.73–3.02(6H, m), 3.26(3H, s), 3.54–4.32(7H, m), 4.57(1H, dd)

IR (KBr, cm$^{-1}$): 3430, 3290, 3190, 2940, 1708, 1631, 1551, 1510, 1449, 1402, 1331, 1065

EXAMPLE 25

7-N-[2-[(γ-L-Glutamyl-L-cysteinyl-ethyl-glycinat-S-yl)thio]ethyl]mitomycin C (Compound 25)

50 mg of γ-L-glutamyl-L-cysteinyl-glycyl ethyl ester hydrochloride (described in Proc. Natl. Acad. Sci., 80, 5258, 1983) is dissolved in ethanol (3 ml). To this solution is added 20 μl of triethylamine. To solution is added dropwise to an ethanol solution (7 ml) containing 7-N-[2-(2-pyridyldithio)ethyl]mitomycin C (70 mg) at room temperature with stirring. Then, the mixture is stirred for 10 minutes. The solvent is removed from the solution under reduced pressure at a temperature not higher than 30° C. The residue is dissolved in a small amount of water. A column packed with Diaion HP 20 (commercial product of Mitsubishi Kasei Kogyo K.K., Tokyo) as a carrier is used to adsorb the active material. After washing with water, elution is effected by using a mixture of water/ethanol (4:6 v/v). Bluish fractions are collected, combined and concentrated under reduced pressure. The concentrate is freeze-dried to obtain 45 mg of Compound 25 as a grayish blue powder (Yield: 44.5%).

Elementary analysis (%): C 47.6, H 5.8, N 13.2 Calculated as $C_{29}H_{41}N_7O_{11}S_2$: C 47.9, H 5.7, N 13.5

MS (by SIMS method, m/z): 730(M$^+$ +3), 729(M$^+$ +2), 728(M$^+$ +1)

$^1$H-NMR (D$_2$O, δ): 1.25(3H, t, J=7.2), 1.98(3H, s), 2.15(2H, m), 2.52(2H, m), 2.97(1H, dd, J=14.3, 9.1), 3.01(4H, m), 3.19(1H, dd, J=14.3, 4.8), 3.28(3H, s), 3.63(1H, dd, J=10.7, 4.6), 3.64(1H, bd, J=13.3), 3.76(1H, t, J=6.4), 3.97 and 4.01 (2H, AB, J=17.7), 4.01(2H, t, J=6.2), 4.18(1H, d, J=13.3), 4.19(2H, q, J=7.2), 4.23(1H, dd, J=10.8, 10.7), 4.58(1H, dd, J=10.8, 4.6), 4.72 (1H, dd, J=9.1, 4.8)

IR (KBr, cm$^{-1}$): 3300, 3070, 2990, 2950, 1715, 1635, 1553, 1513, 1450, 1330, 1212, 1065

EXAMPLE 26

7-N-[2-[γ-L-Glutamyl-L-cysteinyl-ethyl-glycinat-S-yl)thio]ethyl]mitomycin D (Compound 26)

A similar procedure to that described in Example 25 is effected by the use of 50 mg of γ-L-glutamyl-L-cysteinyl-glycyl ethyl ester hydrochloride and 70 mg of 7-N-[2-(2-pyridyldithio)ethyl]mitomycin D to obtain 39 mg of Compound 26 as a grayish green powder (Yield: 38.6%).

Elementary analysis (%): C 47.6, H 5.8, N 13.2 Calculated as $C_{29}H_{41}N_7O_{11}S_2$: C 47.9, H 5.7, N 13.5

MS (by SIMS method, m/z): 731(M$^+$ +4), 730(M$^+$ +3), 729(M$^+$ +2), 728(M$^+$ +1)

$^1$H-NMR (D$_2$O, δ): 1.25(3H, t, J=7.1), 1.97(3H, s), 2.14(2H, m), 2.30(3H, s), 2.51(2H, m), 2.59(1H, d, J=4.8), 2.70(1H, dd, J=4.8, 2.1), 2.98(1H, dd, J=14.2, 9.2), 3.00(2H, m), 3.20(1H, dd, J=14.2, 4.9), 3.65(1H, dd, J=13.6, 2.1), 3.72(1H, dd, J=9.4, 3.6), 3.76(1H, t, J=6.4), 3.98 and 4.01(2H, AB, J=17.7), 4.01(2H, t, J=6.2), 4.07 (1H, d, J=13.6), 4.20(2H, q, J=7.1), 4.38(1H, dd, J=10.8, 9.4), 4.68(1H, dd, J=10.8, 3.6), 4.72(1H, dd, J=9.2, 4.9), IR (KBr, cm$^{-1}$): 3290, 2990, 1709, 1632, 1548, 1512, 1336, 1210

EXAMPLE 27

7-N-[2-(4-Acetamidophenyldithio)ethyl]mitomycin E (Compound 27)

A similar procedure to that described in Example 1 is effected using 70 mg of 7-N-[2-(2-pyridyldithio)ethyl]mitomycin E (disclosed in EP 00116208 A1) and 22 mg of 4-mercaptoacetanilide to obtain 71.9 mg of compound 27 as a grayish blue powder with a yield of 92.7%.

Elementary analysis (%): C 54.1, H 5.2, N 11.9 Calculated as $C_{26}H_{31}N_5O_6S_2$: C 54.4, H 5.5, N 12.2

$^1$H-NMR (CDCl$_3$, δ): 1.87(3H, s), 2.16(3H, s), 2.33 (1H, d), 2.33(3H, s), 2.38(1H, dd), 2.93(2H, t), 3.30(3H, s), 3.57(1H, dd), 3.75(2H, q), 3.79 (1H, dd), 4.03(1H, d), 4.40(1H, dd), 4.75(2H, br.), 4.82(1H, dd), 6.24(1H, br.), 7.48(4H, s), 8.52(1H, br.)

IR (KBr, cm$^{-1}$): 3300, 2940, 1710, 1680, 1633, 1590, 1550, 1510, 1446, 1397, 1330, 1312, 1051, 758

EXAMPLE 28

7-N-[2-(D-Penicillamin-S-yl)thio]ethyl]mitomycin C (Compound 28)

A similar procedure to that described in Example 14 is effected using 70 mg of 7-N-[2-(2-pyridyldithio)ethyl]mitomycin C and 20 mg of D-penicillamine to obtain 61.6 mg of compound 28 as a grayish green powder with a yield of 81.8%.

EXAMPLE 29

The various compounds of formula (I) of the preceding examples were subjected to thin layer chromatography to obtain Rf values. The results are shown in the following Tables 2 and 3. The values given in these tables were obtained using thin layer chromatography plates Art. 5729, 60F$_{254}$ and Arf. 15685, RP-18 F$_{254}$-S (Merck AG.) respectively.

TABLE 2

Rf values of compounds of formula (I) obtained by TLC
A: Compound No., B: ethyl acetate/acetone (7:3 v/v)
C: chloroform/methanol (9:1 v/v)

| A | B | C | A | B | C |
|---|---|---|---|---|---|
| 1 | 0.39 | 0.46 | 10 | 0.35 | 0.38 |
| 2 | 0.29 | 0.32 | 11 | 0.49 | 0.61 |
| 3 | 0.24 | 0.51 | 12 | 0.37 | 0.65 |
| 4 | 0.26 | 0.50 | 13 | 0.38 | 0.39 |
| 5 | 0.13 | 0.20 | 16 | * | 0.21 |
| 6 | 0.38 | 0.52 | 17 | * | 0.22 |
| 7 | 0.18 | 0.33 | 27 | 0.21 | 0.33 |
| 8 | 0.32 | 0.67 | MM-A | 0.30 | 0.34 |
| 9 | 0.32 | 0.67 | | | |

*not measured

TABLE 3

Rf values of compounds of formula (I) obtained by TLC
(methanol/water = 6:4 v/v)

| Compound No. | Rf | Compound No. | Rf |
|---|---|---|---|
| 14 | 0.54 | 21 | 0.49 |
| 15 | 0.61 | 22 | 0.70 |
| 18 | 0.49 | 23 | 0.75 |
| 19 | 0.67 | 24 | 0.46 |
| 20 | 0.44 | 25 | 0.36 |
| | | 26 | 0.47 |

EXAMPLE 30

The various compounds of formula (I) of Examples 1–26 were tested for antibacterial activity against 6 microorganisms. Table 4 shows the minimum growth inhibitory concentrations (MIC) (mcg/ml), determined by the agar dilution method at a pH of 7.0. In this table, the following symbols are used:

SF: *Streptococcus faecalis* ATCC 10541
SA: *Staphylococcus aureus* ATCC 6538P
BS: *Bacillus subtilis* 10707
PV: *Proteus vulgaris* ATCC 6897
SS: *Shigella sonnei* ATCC 9290
KP: *Klebsiella pneumoniae* ATCC 10031
MM-C: Mitomycin C

TABLE 4

| Compounds | Antibacterial activity (MIC ... mcg/ml) | | | | | |
|---|---|---|---|---|---|---|
| | SF | SA | BS | PV | SS | KP |
| 1 | 0.02 | 0.02 | <0.01 | 1.3 | 20 | 0.31 |
| 2 | <0.02 | 0.04 | <0.02 | 2.5 | 20 | 0.31 |
| 3 | 0.04 | 0.08 | <0.01 | 5.0 | 20 | 0.63 |
| 4 | 0.04 | 0.08 | 0.02 | 5.0 | >20 | 1.3 |
| 5 | 0.04 | 0.02 | 0.005 | 5.0 | >40 | 0.16 |
| 6 | 0.63 | 1.3 | 0.08 | | | >20 |
| 7 | 5.0 | 10 | 5.0 | >40 | | |
| 8 | 0.16 | 0.16 | 0.08 | 2.5 | 5.0 | 1.3 |
| 9 | <0.02 | <0.02 | <0.02 | 1.3 | 40 | 0.63 |
| 10 | 0.08 | 0.04 | 0.02 | 2.5 | >20 | 1.3 |
| 11 | 0.04 | <0.01 | <0.01 | 0.63 | 10 | 0.63 |
| 12 | <0.02 | <0.02 | <0.02 | 0.63 | 20 | 0.31 |
| 13 | 0.31 | 0.16 | 0.02 | 5.0 | 10 | 0.63 |
| 14 | 0.31 | 0.31 | 0.16 | 5.0 | >20 | 0.63 |
| 15 | 13 | 13 | 6.3 | 13 | | |
| 16 | 0.39 | 0.20 | <0.02 | 1.6 | 50 | 0.20 |
| 17 | 0.20 | 0.20 | <0.02 | 1.6 | 25 | 0.20 |
| 18 | 0.63 | 0.31 | 0.08 | 0.31 | >20 | 0.08 |
| 19 | 1.3 | 0.63 | 0.08 | 2.5 | >20 | 0.63 |
| 20 | 0.63 | 0.31 | 0.08 | 5.0 | | 0.63 |
| 21 | 13 | 13 | 3.1 | 13 | | |
| 22 | 1.3 | 0.31 | 0.08 | 2.5 | >20 | 0.63 |
| 23 | 6.3 | 6.3 | 6.3 | 13 | | |
| 24 | 0.63 | 0.08 | <0.02 | 1.3 | 40 | 0.31 |
| 25 | 0.63 | 0.16 | 0.04 | 10 | | 2.5 |
| 26 | 13 | 6.3 | 1.6 | 13 | 25 | |
| MM-C | 0.04 | 0.02 | 0.01 | 0.04 | 1.3 | <0.01 |

EXAMPLE 31

The antitumour-activity and toxicity of various compounds of formula (I) were investigated as indicated below. The results are given in Table 5.

(1) Effect against Sarcoma 180 solid tumour cells $5 \times 10^6$ cells of Sarcoma 180 solid tumour were intraperitoneally implanted into ddy mice. 7 days later, ascites cells were sampled. The cells were washed once with a sterilized physiological solution of sodium chloride and were used to prepare a cell suspension containing $5 \times 10^7$ cells per ml. On each occasion, 0.1 ml of the cell suspension was subcutaneously implanted into the right arm pit of a male mouse (ddy strain; body weight $20 \pm 2$ g). The test compound was dissolved in a physiological solution of sodium chloride with or without addition of Tween 80 and was administered into the tail vein of each mouse of a group consisting of 5 mice at a dose of 0.1–0.2 ml, 24 hours after the implantation of the tumour cells.

The anti-tumour activity was determined in the following manner. 7 days after the implantation, the major axis (a) and the minor axis (b) of the tumour were measured to calculate a value of "$a \times b^2/2$" which corresponds to the volume of the tumour. The anti-tumour activity was expressed by the ratio of the volume of the tumours (T) of the group of animals administered with the test compound to the corresponding volume of tumours (c) of the untreated animals.

(2) Determination of $ED_{50}$ (The amount needed for reducing the volume of Sarcoma 180 solid tumours in mice to 50% on the basis of the corresponding volume of Sarcoma solid tumours in control untreated animals). On graph paper, T/C (the ratio of the volume of tumours of treated and control animals) was indicated by an arithmetic scale on the longitudinal axis and the administered amount of the test compound was indicated by a logarithmic scale on the lateral axis.

The relationship between the dose and T/C was shown by a straight line determined by the method of least squares, from which a dose corresponding to T/C of 0.5 was obtained.

(3) Acute toxicity

Each animal of the test group consisting of 5 ddy mice was administered intraperitoneally once with a test compound. After this, the animals were observed for 14 days and deaths were noted. The $LD_{50}$ was determined by Behrens Kerber's method.

(4) Effect on the peripheral leucocytes number

Sarcoma 180 solid tumour cells ($5 \times 10^6$) were subcutaneously implanted into the right arm pit of each mouse (body weight $20 \pm 2$ g) of a group consisting of 5 male mice (ddy strain). 24 hours after implantation, a test compound was intraperitoneally administered to each animal. 4 days later, blood (each 0.02 ml) was collected from the suborbital plexus vein of each tumour-carrying animal. The collected sample of the blood was dispersed in 9.98 ml of Cell-Kit Seven solution. One drop of saponin solution was added to the sample to dissolve erythrocytes, and then a microcell counter was used to measure the number of leucocytes. On a graph paper, the number of leucocytes was indicated on the y-axis by an arithmetic scale and the dose of the test compound was indicated on the x-axis by a logarithmic scale. The relationship between the number of peripheral leucocytes and the dosage of the test compound was plotted and the dosage corresponding to 4000 peripheral leucocytes/mm³ (about ½ the number of leucocytes of normal mice) was obtained. This value is denoted in Table 5 by $WBC_{4000}$.

TABLE 5

Anti-tumour activity against Sarcoma 180 solid tumour and toxicity of various compounds of formula (I)
No.: Compound No., A: $LD_{50}$ (mg/kg), B: $ED_{50}$ (mg/kg), C: $WBC_{4000}$ (mg/kg)

| No. | A | B | C |
|---|---|---|---|
| 3 | 7.5 | 5.0 | >10 |
| 4 | 9.0 | 5.1 | >10 |
| 5 | 30.0 | 8.5 | 14.2 |
| 7 | 46.3 | >25 | 45.5 |
| 9 | 5.3 | 7.4 | >10 |
| 11 | 9.0 | 4.5 | >10 |
| 12 | 6.8 | 3.5 | 10.4 |
| 14 | 30 | 15.4 | 26.9 |
| 15 | 135 | 54.0 | 81.9 |
| 18 | 30 | 9.9 | 18.8 |
| 20 | 27.0 | 9.6 | 20.5 |
| 21 | >200 | 61.1 | 83.9 |

TABLE 5-continued

Anti-tumour activity against Sarcoma 180 solid tumour and toxicity of various compounds of formula (I)
No.: Compound No., A: $LD_{50}$ (mg/kg), B: $ED_{50}$ (mg/kg), C: $WBC_{4000}$ (mg/kg)

| No. | A    | B   | C    |
| --- | ---- | --- | ---- |
| 28  | 26.3 | 8.2 | 16.3 |

EXAMPLE 32

The solubilities of Compound 5, Compound 14 and Compound 20 in 0.03M phosphate buffered solution (pH 7.0, 23° C.) were determined. The results are given in the following Table 6.

TABLE 6

| Compound No. | 5         | 14         | 20         |
| ------------ | --------- | ---------- | ---------- |
| Solubility   | 52 mcg/ml | >100 mg/ml | >100 mg/ml |

EXAMPLE 33

10 g of Compound 3 is dissolved in 1000 ml of ethanol. The solution is sterilized using a Millipore filter (pore size: 0.22μ) under pressure. The filtrate is divided into small fractions and poured into brown vials (1.0 ml per vial; active principle 10 mg per vial) and frozen for 2 hours at −50° C., followed by a primary drying in vacuo (0.1 mm Hg) for 24 hours at −10° C. After confirming that the rack temperature is the same as the material temperature, a secondary drying is effected in vacuo (0.1 mm Hg) at a rack temperature of 20° C. for 4 hours. Each vial is sealed with a rubber stopper to obtain an injection agent. In use, 5 ml of a sterilized physiological solution of sodium chloride containing a dissolving promotor is put into each vial, which is dissolved by stirring thoroughly to obtain an injectable preparation.

EXAMPLE 34

3 g of Compound 11 is dissolved in 1000 ml of distilled water. The solution is sterilized by the use of a Millipore filter (pore size: 0.22μ) under pressure. The sterile filtrate is divided into fractions and poured into brown vials (each 1.0 ml per vial; active principle 3 mg per vial). The vials are frozen at −50 C. for 2 hours, and a primary drying is effected in vacuo (0.1 mmHg) for 24 hours at a rack temperature of −10° C. After confirming that the rack temperature is the same as the material temperature, a secondary drying is effected in vacuo (0.1 mmHg) for 4 hours at a rack temperature of 30° C. to remove moisture. Each vial is then sealed with a rubber stopper. In use, 5 ml of a sterilized physiological solution of sodium chloride is poured into each vial. The vial is shaken to dissolve the ingredient. In this manner, an injectable preparation is prepared.

EXAMPLE 35

Tablets are prepared in conventional manner by the use of 10 mg of Compound 20, 90 mg of lactose, 40 mg of corn starch, 4 mg of polyvinyl alcohol, 28 mg of Avicel and 1 mg of magnesium stearate per tablet.

We claim:

1. Mitomycin derivatives of general formula (I)

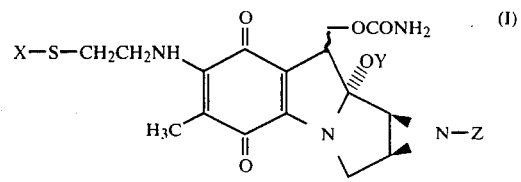

wherein Y and Z; which may be the same or different, each represents a hydrogen atom or a methyl group; ⁓represents α or β bonding and x represents a group of formula (II)

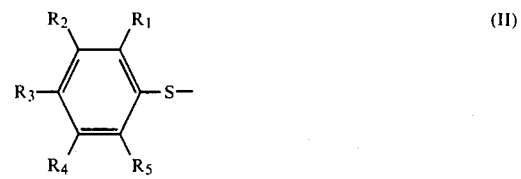

wherein $R_1$ to $R_5$ are each selected from hydrogen, halogen, hydroxyl, nitro, amino, lower alkyl, lower alkoxy, lower alkylamino or lower alkanoylamino, and salts thereof.

2. Mitomycin derivatives of general formula (I) as claimed in claim 1 wherein Y, Z and ⁓ are as defined in claim 1 and X is a group of formula (II)

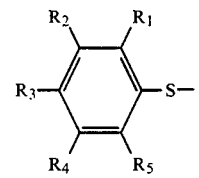

wherein (a) either one of $R_1$ to $R_5$ or two of $R_1$ to $R_5$, which may be the same or different, is/are selected from hydroxy, nitro, amino, lower alkyl, lower alkoxy, lower alkylamino or lower alkanoylamino and the remaining R groups are hydrogen atoms; or (b) one or more of $R_1$ to $R_5$ are halogen atoms and any remaining R groups are hydrogen atoms, and salts thereof.

3. A mitomycin derivative as claimed in claim 2 selected from 7-N-[2-(4-acetamidophenyldithio)ethyl]-mitomycin C, 7-N-[2-(4-acetamidophenyldithio)ethyl]-mitomycin D, 7-N-[2-(4-nitrophenyldithio)ethyl]mitomycin C, 7-N-[2-(4-fluorophenyldithio)ethyl]mitomycin C, 7-N-[2-(2,3,5,6-tetrafluorophenyldithio)ethyl]-mitomycin C and 7-N-[2-(4-acetamidophenyldithio)ethyl]mitomycin E.

4. A pharmaceutical composition containing as active ingredient at least one mitomycin derivative of general formula (I), as defined in claim 1 or a physiologically acceptable salt thereof in association with a pharmaceutical carrier.

5. A composition according to claim 4 having an effective amount of said mitomycin derivative to have antibacterial or anti-tumour effectiveness.

* * * * *